(12) United States Patent
Kaufmann (10) Patent No.: US 6,885,453 B2
(45) Date of Patent: **\*Apr. 26, 2005**

(54) GAS PERMEABLE PROBE FOR USE IN AN OPTICAL ANALYZER FOR AN EXHAUST GAS STREAM FLOWING THROUGH A DUCT OR CHIMNEY

(75) Inventor: Jürgen Kaufmann, Waldkirch (DE)

(73) Assignee: Sick AG, Waldkirch (DE)

( * ) Notice: Subject to any disclaimer, the term of this patent is extended or adjusted under 35 U.S.C. 154(b) by 151 days.

This patent is subject to a terminal disclaimer.

(21) Appl. No.: 10/054,516

(22) Filed: Nov. 13, 2001

(65) Prior Publication Data

US 2003/0090667 A1 May 15, 2003

(51) Int. Cl.[7] .............................................. G01N 21/61
(52) U.S. Cl. ....................................... 356/439; 250/573
(58) Field of Search ................................ 356/437, 438, 356/439; 250/338.5, 343, 573

(56) References Cited

U.S. PATENT DOCUMENTS

| | | | |
|---|---|---|---|
| 4,549,080 A | * | 10/1985 | Baskins et al. ............. 250/343 |
| 4,560,873 A | | 12/1985 | McGowan et al. |
| 6,064,488 A | | 5/2000 | Brand et al. |

\* cited by examiner

Primary Examiner—Richard A. Rosenberger (74) Attorney, Agent, or Firm—Townsend and Townsend and Crew LLP (57) ABSTRACT

A gas permeable probe for use in an optical analyzer for an exhaust gas stream flowing through a duct or chimney has:

an elongate hollow structure having first and second ends and a side wall, with an optical cavity defined between the first and second ends within the side wall, a filter forming part of the elongate hollow structure, a mounting structure at the first end and adapted for mounting the elongate hollow structure within the duct or chimney, an optical window at the first end permitting a light beam originating from an optical analyzer to enter into the optical cavity to travel from the first end to the second end, a retroreflector provided at the second end for returning the light beam to the first end of the hollow structure, and a tube disposed within the mounting structure and having first and second opposite ends, the first opposite end being located remote from the first end of the elongate hollow structure and being closed by a first window adapted to transmit the light beam from an optical analyzer into the tube and the second end of the tube being closed by a second window adapted to transmit the beam of light from the tube into the optical cavity and the returned light beam from the optical cavity into the tube, the tube thereby defining a closed cavity, the closed cavity being one of an evacuated cavity and a cavity containing a neutral gas.

10 Claims, 6 Drawing Sheets

GAS PERMEABLE PROBE FOR USE IN AN OPTICAL ANALYZER FOR AN EXHAUST GAS STREAM FLOWING THROUGH A DUCT OR CHIMNEY

BACKGROUND OF THE INVENTION

The present invention relates to a gas permeable probe for use in an optical analyzer for an exhaust gas stream flowing through a duct or chimney, the probe comprising:
an elongate hollow structure having first and second ends and a side wall, with an optical cavity defined between the first and second ends within the side wall,
a filter forming part of the elongate hollow structure,
a mounting structure at the first end and adapted for mounting the elongate hollow structure within the duct or chimney,
an optical window at the first end permitting a light beam originating from an optical analyzer to enter into the optical cavity to travel from the first end to the second end, and
a retroreflector provided at the second end for returning the light beam to the first end of the hollow structure.

A gas permeable probe of this kind is known, for example, from U.S. Pat. No. 4,560,873. The gas permeable probe disclosed in this reference utilizes a cylindrical ceramic filter to permit gas flowing through the chimney to enter into the optical cavity, with the pores of the filter being sized such that particulate material in the chimney is prevented from entering the optical cavity. A similar gas permeable probe is disclosed in U.S. Pat. No. 6,064,488 in which the elongate hollow structure comprises a tube having slots relieved in the upper and lower surfaces thereof. Filters of sintered metal are welded into the resulting windows to allow gas flowing through a chimney to enter into the optical cavity. The porosity, area and location of the filters in the known arrangements determine the rate at which gas diffuses through the optical cavity. Gas permeable probes of the above kind are used in optical analyzers designed to carry out spectral analysis of gases contained in the optical cavity. Since the gases contained in the optical cavity connected to the gases flowing through the duct or chimney it is possible, using a spectral analyzer, to obtain information on the type of gas that are present in the duct or chimney and their relative concentrations.

Moreover, a gas permeable probe of this kind can also be used to obtain information on various types of dust and dust contents in gas flows such as exhaust streams. This can be done if the pore size of the filter is selected such that the dust of interest can enter into and escape from the optical cavity.

Gas permeable probes of the kind to which the present application relates can be used in gas carrying ducts, especially exhaust ducts of all kinds which operate in a temperature range of e.g. 50° C. to 450° C. Such ducts are, for example, found in power stations, refuse burning plants, in cement works, in association with large furnaces, in steelworks and in gasworks.

In the gas permeable probe known from U.S. Pat. No. 4,560,873 the optical window takes the form of a field lens and it may be provided with a sealing means such as an O-ring to isolate the optical cavity from the rest of the system. A system is provided for continuously supplying a purging gas to a hollow structure provided between the transceiver of the optical analyzer and the lens to keep this hollow structure and the transceiver free of stack gases, i.e. gases flowing through the duct or chimney, and any other contaminated gases. In this way the transmission of light from and to the transceiver will not be undesirably attenuated by unwanted and unknown gases and therefore not give false signals.

However, this system is very wasteful since it requires a continuous supply of purging gas and indeed over a potentially very long period of time. Moreover, the purging gas must be kept free of contaminants, such as dust, lubricating oil and water vapor, because otherwise the optical elements in the transceiver and the above-mentioned lens could still become contaminated with dust, oil, an emulsifier of oil in water or simply by condensation, which would all undesirably affect the quality of the measurement and require periodic cleaning.

SUMMARY OF THE INVENTION

An object of the present invention is to provide a gas permeable probe of the above-mentioned kind which essentially fully eliminates problems with contamination of the optical system outside of the optical cavity and thus avoids the need for frequent cleaning of the optical system and which indeed essentially requires no cleaning at all.

In order to satisfy these objects there is provided a gas permeable probe for use in an optical analyzer for an exhaust gas stream flowing through a duct of chimney, the probe comprising:
an elongate hollow structure having first and second ends and a side wall, with an optical cavity defined between the first and second ends within the side wall,
a filter forming part of the elongate hollow structure,
a mounting structure at the first end and adapted for mounting the elongate hollow structure within the duct or chimney,
an optical window at the first end permitting a light beam originating from an optical analyzer to enter into the optical cavity to travel from the first end to the second end,
a retroreflector provided at the second end for returning the light beam to the first end of the hollow structure, and
a tube disposed within the mounting structure and having first and second opposite ends, the first opposite end being located remote from the first end of the elongate hollow structure and being closed by a first window adapted to transmit the light beam from an optical analyzer into the tube and the second end of the tube being closed by a second window adapted to transmit the beam of light from the tube into the optical cavity and the returned light beam from the optical cavity into the tube, the tube thereby defining a closed cavity, the closed cavity being one of an evacuated cavity and a cavity containing a neutral gas.

Since the tube is sealed at the one end by the optical window and at the other end by a further optical window, the space within the tube cannot be contaminated, either by gases flowing through the duct or chimney or as a result of external effects. Moreover, since the tube may be evacuated or alternatively contains a neutral gas or a neutral gas mixture it cannot impair a measurement carried out using the gas permeable probe.

In a preferred embodiment the second window is formed by the optical window at the first end of the optical cavity. This minimizes the number of boundary surfaces that is present and avoids the problem of possible ingress of contamination between the optical window and an adjacent end window of the tube, since an adjacent window is not present.

The mounting structure preferably comprises a first mounting flange at the first end of the elongate hollow structure, the first mounting flange containing the optical window, and the probe preferably further comprises a mating flange secured to the second opposite end of the tube and sealingly connected to the first mounting flange. This represents a reliable design for attaching the optical window to the end of the tube.

A ring-shaped connecting member is conveniently disposed between the first mounting flange and the mating flange, and a ring heater is disposed around the connecting member. The mating flange is then connected to the connecting member and the first mounting flange is connected to the connecting member. This design not only permits adequate sealing, it also ensures condensation does not occur at the optical window, which is a particular danger if the temperature of the window is lower than that of the gases flowing through the duct or chimney.

Respective seals are usefully provided between the mating flange and the ring heater, between the ring heater and the connecting member, between the connecting member and the first mounting flange and between the first mounting flange and the optical window. These seals ensure the inside of the tube remains sealed against the external environment.

The mounting structure expediently comprises a first mounting flange at the first end of the elongate hollow structure, a second mounting flange adapted for mounting to a wall of the duct of the chimney and a support tube extending from the second mounting flange to the first mounting flange. Thus the sealed tube is surrounded in the duct or chimney by a support tube and protected from hot and possibly corrosive gases in the duct or chimney. The support tube therefore not only mechanically supports the optical window, the filter and the retroreflector, it also protects the sealed tube, preventing mechanical deflection thereof and deterioration of the seals, all of which helps ensure the sealed tube does not undesirably affect the quality of the measurement.

A carrier for an optical analyzer is preferably provided which extends away from the second mounting flange, at a side of the second mounting flange remote from the first mounting flange, to a third mounting flange at the first opposite end of the sealed tube, with the third mounting flange being adapted for the attachment of an optical analyzer positioned outside of the duct or chimney. This arrangement permits the optical analyzer, or at least the transceiver thereof, to be mounted in a sealed manner at the end of the sealed tube outside of the duct or chimney and thus ensures contamination cannot enter the transceiver at this point and also prevents contamination of the optical window at this end of the sealed tube.

A housing is usually provided on the carrier for the optical analyzer and contains at least one of:

a power supply including a lead for at least one heater associated with the gas measurement probe, a regulating circuit for regulating an operation of the at least one heater, at least one gas supply line for supplying at least one of a calibration gas, a neutral gas and a filter cleaning gas to the optical cavity, at least one pressure sensing line for sensing an operating pressure in or adjacent to the optical cavity, and at least one temperature sensing line for sensing an operating temperature in or adjacent to the optical cavity. These items are thus also housed in a manner which protects them against contamination.

Moreover, an intermediate space is preferably formed between the support tube and the tube, and all lines and leads associated with the gas measurement probe and extending to the first end of the elongate hollow structure or beyond the fist end are routed through this intermediate space. This prevents the possibility of the lines and leads giving rise to contamination which can enter the sealed tube. Even if contamination should arise, for example due to volatile substances present on or in the lines or leads, it is prevented from entering the sealed tube and is retained in the intermediate space.

Further advantages of the invention will be set forth in the subsequent description given with reference to the preferred embodiments as illustrated in the drawings.

DESCRIPTION OF THE PREFERRED EMBODIMENTS

Figure 1:
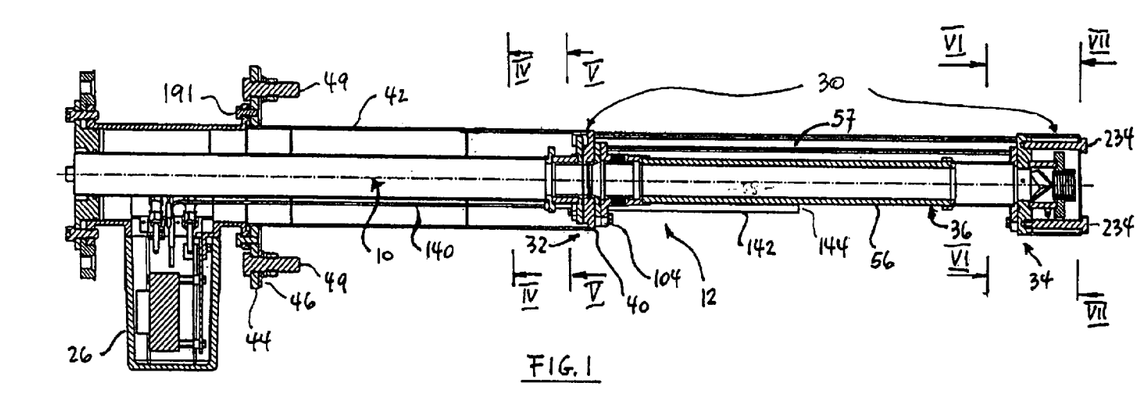
FIG. 1 is a schematic axially sectioned view of a gas permeable probe made in accordance with the present invention taken along line I—I in FIGS. 4 to 7, FIGS. 1A–1C show sequential axial sections of the representation of FIG. 1 to an enlarged scale.
Figure 1A:
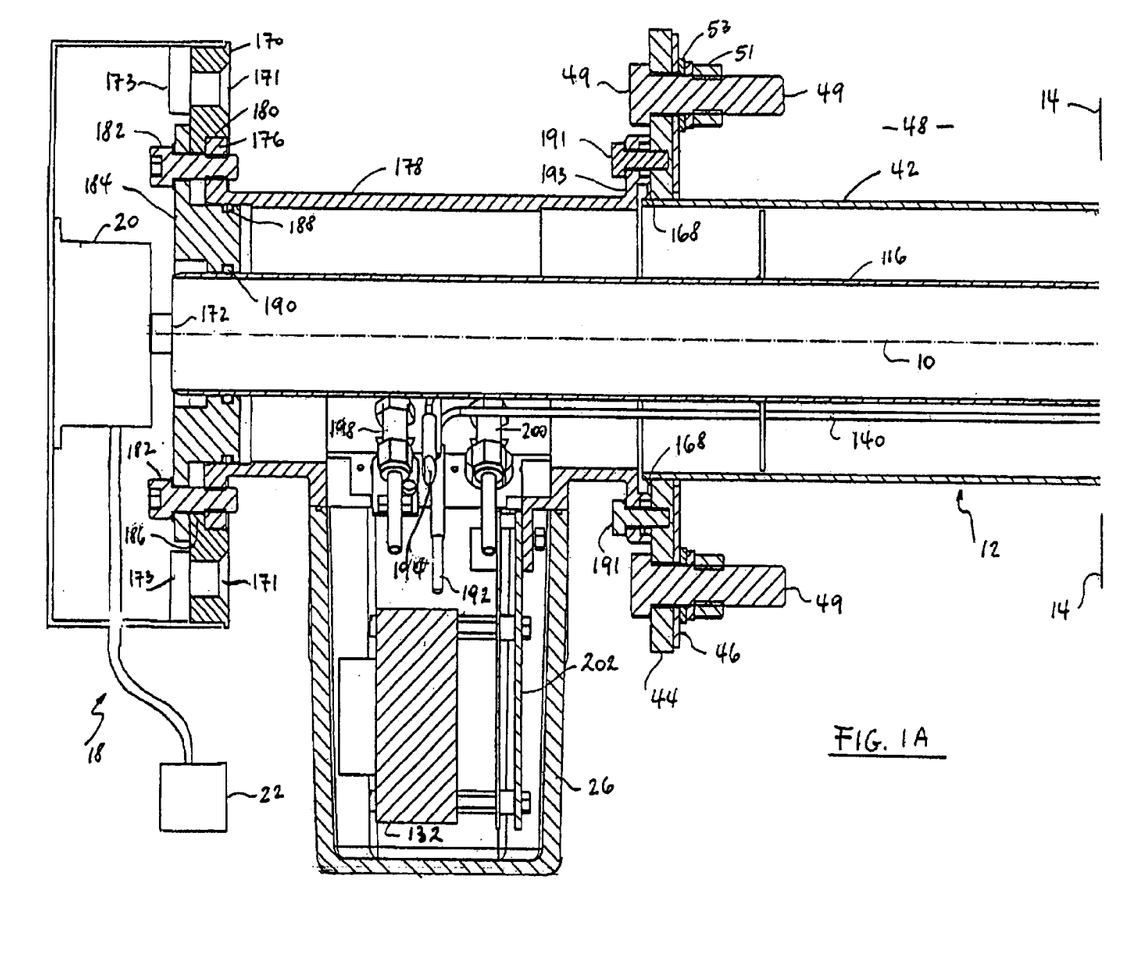
Figure 1B:
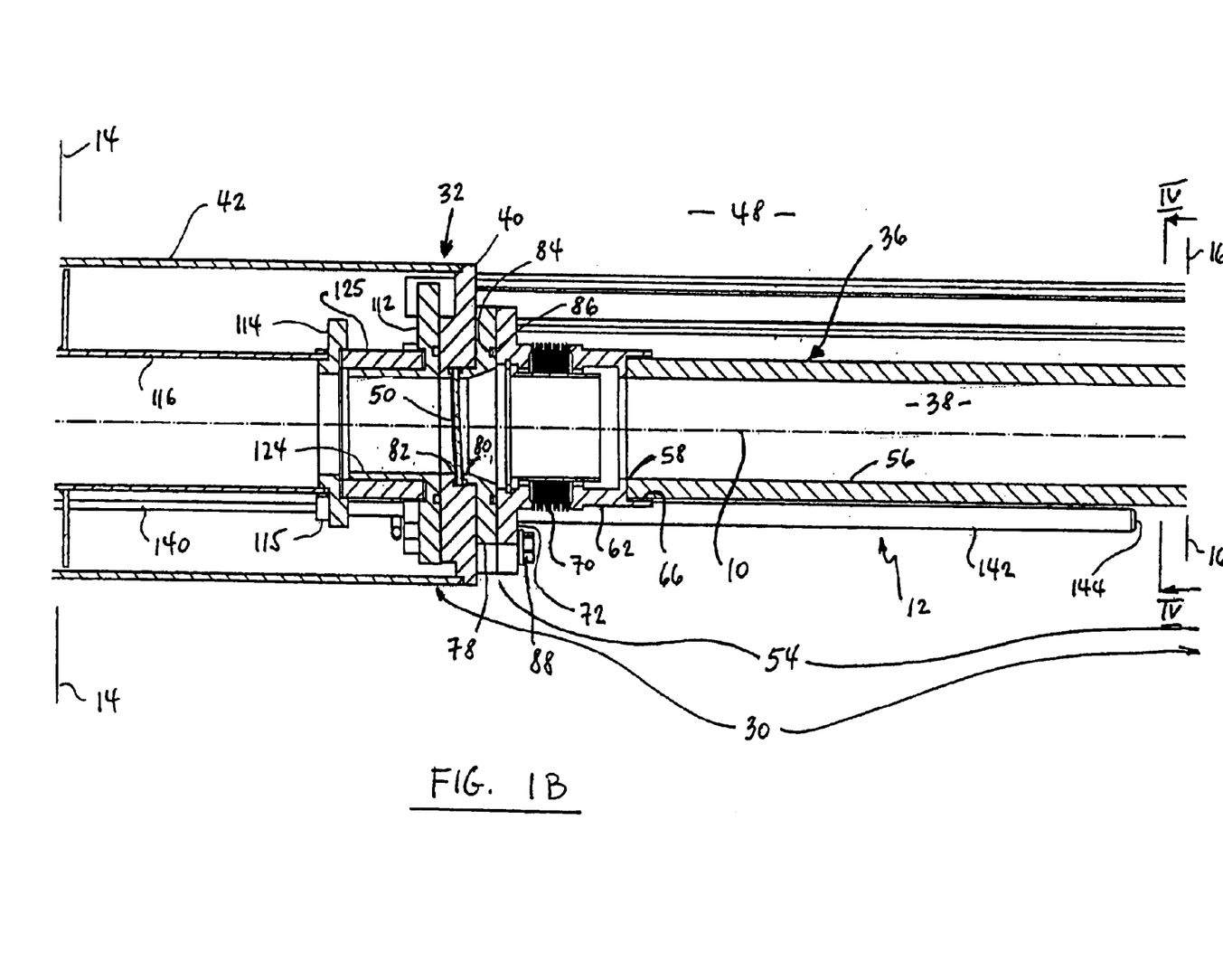
Figure 1C:
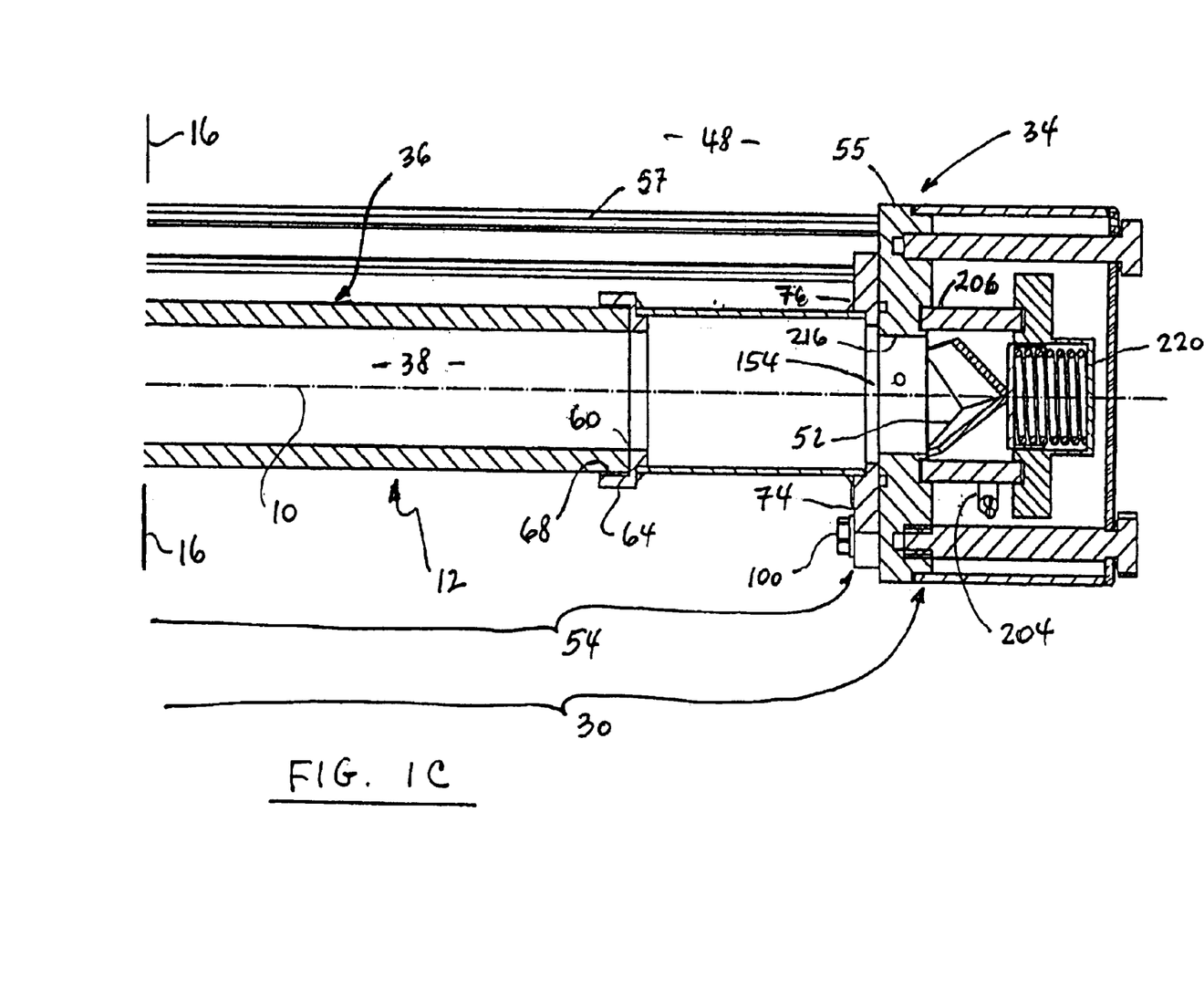

Turning first of all to FIG. 1, there can be seen an axial section along the axis 10 of a gas permeable probe indicated generally by the reference numeral 12. FIGS. 1A, 1B and 1C then show three sequential sections of the representation of FIG. 1 to an enlarged scale. The three sections of FIGS. 1A, 1B and 1C have been formed such that the position 14 at the right-hand end of FIG. 1A corresponds to the position 14 at the left-hand end of FIG. 1B and such that the position 16 at the right-hand end of FIG. 1B corresponds to the position 16 at the left-hand end of FIG. 1C.

The gas permeable probe 12 is used with an optical analyzer indicated generally by the arrow 18, which is only schematically illustrated at the left-hand end of FIG. 1A but not in FIG. 1. The optical analyzer 18 comprises a light emitter and receiver 20, a transceiver located at the left-hand end of the gas permeable probe 12 and an electrical evaluation circuit 22 which is disposed remote from the transceiver 20 in this example but which could also be combined with it. The optical analyzer includes power supplies and other items disposed within the housing 26 as will be explained later in more detail. The optical analyzer can be of any known design.

Figure 6:
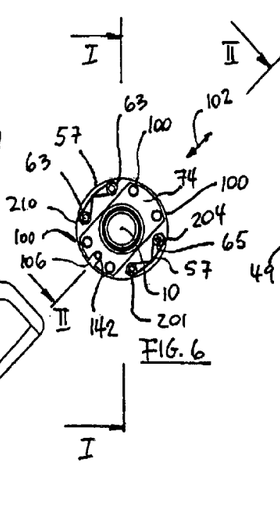
Figure 7:
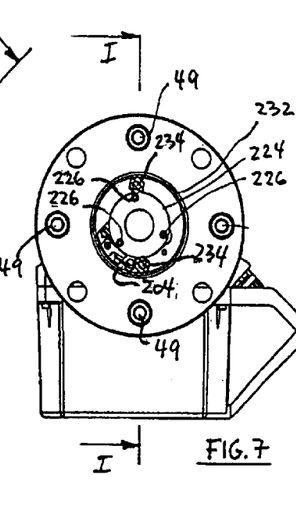

The gas permeable probe of the present invention comprises an elongate hollow structure identified generally by the reference numeral 30 in FIGS. 1B and 1C. The elongate hollow structure 30 has a first end 32 which can be seen in FIG. 1B and a second end 34 identified in FIG. 1C. The elongate hollow structure 30 has a side wall indicated generally at 36 and a hollow optical cavity 38 defined between the first and second ends 32, 34 within the side wall 36. A mounting flange 40 is provided at the first end 32 and forms part of a mounting structure including a support tube 42 and a second mounting flange 44 adapted for mounting the elongate hollow structure 30 to the wall 46 at one side of a duct 48. This connection is effected by bolts 49 which engage into nuts 51 mounted on a ring 53 fixed to the inside of the duct. A support member 55 provided at the second end 34 of the elongate hollow structure is permanently connected to the first mounting flange 40 by a connecting structure comprising two tie members 57 of which only one can be seen in FIG. 1. Both members 57 are shown in FIG. 6.

The gas permeable probe is thus arranged in the duct 48 for carrying out measurements on a gas stream flowing through the duct in the general direction of the arrow 49. An optical window 50 is provided at the first end 32 of the elongate hollow structure 30 and permits a beam of light (not shown) originating from the transceiver 20 to enter into the optical cavity 38 to travel in a direction generally along the longitudinal axis 10 from the first end 32 to the retroreflector 52 provided at the second end 34 of the elongate hollow structure on the support member 55. The elongate hollow structure includes a filter structure identified generally by the reference numeral 54 which includes, in this embodiment, a tube 56 of filter material having first and second ends 58, 60. The end 58 of the tube 56 of filter material is connected, for example by brazing, to a filter mounting tube 62, and the second end of the tube 56 of filter material is connected to a filter support tube 64. This connection can again be effected by brazing. The tube 56 of filter material can either be a filter of sintered metal or a filter of ceramic material and in either case it is possible to find a braze which is suitable for connecting the two ends 58 and 60 of the tube of filter material to the metallic filter mounting tube 62 and to the metallic filter support tube 64.

Alternatively, these connections can be formed as screw connections, or as adhesively bonded connections, or as interference connections. Irrespective of the type of connection used, it is convenient for the respective first and second ends 58 and 60 of the tube of filter material 56 to be received in ring recesses 66 and 68 provided in the right-hand end of the filter mounting tube 62 and in the left-hand end of the filter support tube 64 respectively.

The left-hand end of the filter mounting tube 62 in FIG. 1B is connected via a flexible metal bellows 70 to a connection flange 72 at the left-hand end of the tubular filter structure 53 in FIG. 1B, and a similar connection flange 74 is provided at the right-hand end of the filter support tube 64 in FIG. 1C. The flexible metallic bellows 70 is connected at its two axial ends to the metallic connection flange 72 and to the filter mounting tube 62 by welding or brazing, and the filter support tube 64 is connected to the connection flange 74 by a welded joint indicated in the usual way by a triangular filter 76 in FIG. 1C. The connection flanges 72 and 74 are both of generally rectangular shape with rounded ends, as can be seen from FIG. 6 for the connection flange 74.

Disposed between the connection flange 72 and the mounting flange 40 is a pressure ring 78 which has a ring-like projection 80 for trapping the optical window 50 between itself and the base of a ring recess 82 provided at the mounting flange 40. A ring groove 84 is provided in the right-hand end face of the pressure ring 78 and accommodates a graphite seal 86 which is compressed when the assembly is bolted together by bolts, such as 88, as can be seen from FIG. 2. A resilient ring seal 83 is provided in a ring groove 85 at the base of the ring recess 82 between the optical window 50 and the ring recess 82. A second ring seal 87 is provided between the ring projection 80 and the optical window 50, in a ring groove 89 in the ring projection 80. These resilient ring seals 83, 87 ensure that the optical window 50 is sealed with respect to both the mounting flange 40 and with respect to the pressure ring 78 and thus with respect to the elongate hollow structure 54. At the same time they ensure that the optical window 50 is not damaged by mechanical pressure exerted between the pressure ring 78 and the mounting flange 40. A graphite seal is provided in a ring groove 79 in the pressure ring 78 to effect a seal between the pressure ring and the connection flange 72.

Within this connection flange 72 and the flexible metallic bellows 70 there is located a sleeve 90. The sleeve 90 is only located at one end 91, between a circlip 93 and a ring shoulder 95, in order that differential thermal expansion and contraction and resilient deflection of the bellows can take place without this affecting the sleeve.

Figure 5:
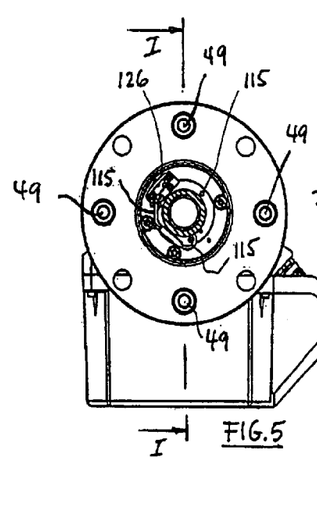

It will be noted from FIGS. 1B and 1C in conjunction with FIG. 6 that the filter module assembly 54 comprising the connection flange 72, the flexible bellows 70, the filter mounting tube 62, the tube of filter material 56, the filter support tube 64 and the connecting flange 74 can be removed from the gas permeable probe by releasing the screws 88 and also the further screws 100 provided at the second end of the elongate hollow structure, which connect the flange 74 to the support member 55. Following the release of the screws 88 and 100 the filter module 54 can be slid sideways, i.e. at right angles to the axial direction 10 out of the assembly, as indicated by the arrow 102 in FIG. 6. The reference numerals 104 and 106 refer to radial slots provided in the connecting flange 72 and in the connecting flange 74 which allow the flange to be passed over a tube 142 which serves for the orientation of the filter module assembly 54 when it is inserted and acts as a stop to ensure it is correctly positioned. At the left-hand side of the mounting flange 40 in FIGS. 1B and 2 there is provided a connecting member 112 which serves for the connection to a mating flange 114 provided at the right-hand end of an inner tube 116 provided coaxially within the support tube 42. This connection is effected by three bolts 115 of which only one is shown in FIGS. 1 and 1B, but which can all be seen in FIG. 5.

The connecting member 112 has an axially projecting sleeve portion 124 which serves to carry a ring-like heater 125 mounted on it and trapped between it and the mating flange 114. The ring-like heater 125 is connected via leads (not shown) to a terminal block 126 provided within the support tube 42 on the mating flange 114, as can be seen from the sectioned drawing of FIG. 2. The terminal block 126 is connected via an electrical lead 128 enclosed within a protective tube 130 extending in the space between the support tube 42 and the inner tube 116 to the power supply 132 provided in the housing 26 shown in FIG. 1A. The purpose of the ring-like heater 124 is to heat the optical window 50, so that at low operating temperatures and with moist gases in the duct or chimney 48 condensation at the optical window 50 is avoided. For this purpose, the temperature of the optical window 50 is held at a temperature above that of the local environment.

Figure 2:
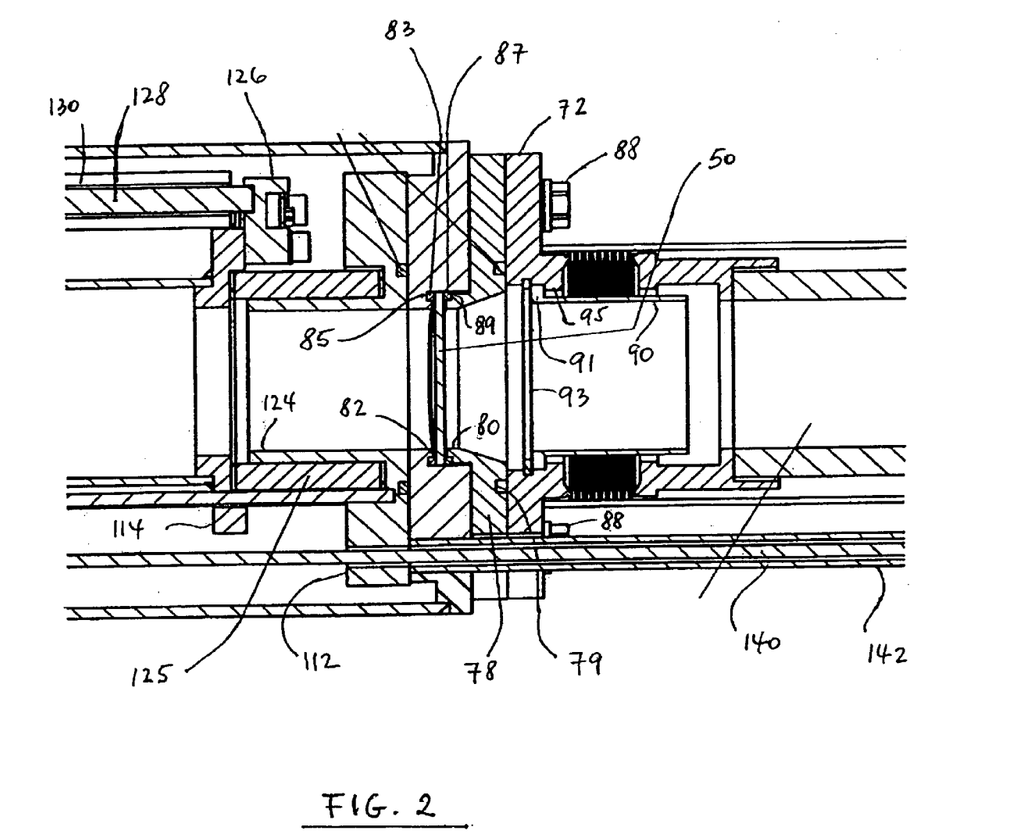
FIG. 2 is a section to a further enlarged scale of the gas permeable probe of the invention in the region of the optical window and the bellows at an orientation around the longitudinal axis taken along line II—II in FIG. 6.

Referring also to FIGS. 1A, 1B and 2, the reference numeral 140 refers to a thermocouple lead which extends in the inner space between the support tube 42 and the inner tube 116 and enters into a protective metallic tube 142 shown in FIG. 1B which terminates at a thermocouple 144 at the right-hand end of FIG. 1B. The thermocouple 144 thus measures the temperature in the duct 48 directly adjacent the surface of the tube of filter material 56 and this temperature can be considered substantially equal to the temperature prevailing in the optical cavity 38. Although not shown in FIGS. 1A and 1B, this tube 142 can also extend through the intermediate space 144 between the support tube 42 and the inner tube 116.

It can also be seen from FIG. 1A that the support tube 42, which is welded to the second mounting flange 44 at the fillet weld 168, terminates essentially at the second mounting flange 44, whereas the inner tube 116 is extended beyond the second mounting flange 44 to a third mounting flange 170 provided at the left-hand end of FIG. 1A. This third mounting flange 170 serves for the attachment of transceiver 20 to the apparatus. This is achieved by screws (not shown) which extend through countersunk bores 171 in the third mounting flange into bores provided in lugs 173 of the transceiver housing. The left-hand end of the inner tube 116 terminates at a window member 172 which does not affect, or at least substantially does not affect, light of the wavelength or wavelengths used for the spectral analysis.

It will be noted that the third mounting flange 170 is connected to a connection flange 176 at the end of a carrier tube 178, which engages into a ring recess 180 in the third mounting flange 170. This connection is effected by means of bolts 182 which pass through a disc member 184 shaped to trap a radially inwardly projecting flange 186 of the third mounting flange 170 between itself and the connection flange 176. The disc member 184 has two O-rings 188, 190 in order to seal the joint between itself and the carrier tube 178 and between itself and the inner tube 116 while permitting relative thermal expansion between the components, which can be taken up by axial sliding between the ring seal 188 and the carrier tube 178 and between the ring seal 190 and the inner tube 116.

The carrier tube 178 is in turn bolted to the second mounting flange 44 by bolts 191 extending through a further connection flange 193 into the second mounting flange. In addition to containing the power supply 132, the housing 26 also contains a connection 192 to the lead 140 leading to the thermocouple 144, a connection 194 to a second thermocouple lead 196, as well as a connection 198 to a pressure transducer provided in the optical cavity and a connection 200 for a tube or line 201 (FIG. 6) for supplying gas to the optical cavity. Since the connection to the line for supplying gas to the optical cavity can be used to supply either a calibration gas, or a natural gas, or a gas used to purge the optical cavity and to clean particulate material from the outside of the tube 56 of filter material, valves (not shown) are provided which allow the respective gases to be admitted to the line 201 as required and which also permit the tube to be isolated relative to the material of the housing, so as to prevent flue gases entering into the housing when no gases are being supplied to the optical cavity via the line 201.

In addition to these items, the housing conveniently contains a circuit board 202 having circuits (not shown) mounted thereon for regulating the supply of electrical energy via the line 128 to the ring heater 125 associated with the optical window 50 and via a line 204 (not shown in FIG. 1A but in FIGS. 1C, 3, 4, 5, 6 and 7) to the similar heater 206 associated with the retroreflector 52. These regulating circuits are designed to regulate the supply of electrical energy to the respective ring heaters 125, 206, taking into account the temperature prevailing in the duct, as measured by the thermocouple 144, and thus taking into account the cooling or heating effect of the gases passing through the duct, so as to maintain temperatures of the optical window and of the retroreflector, which can be preset temperatures, sufficient to ensure condensation does not occur.

Figure 3:
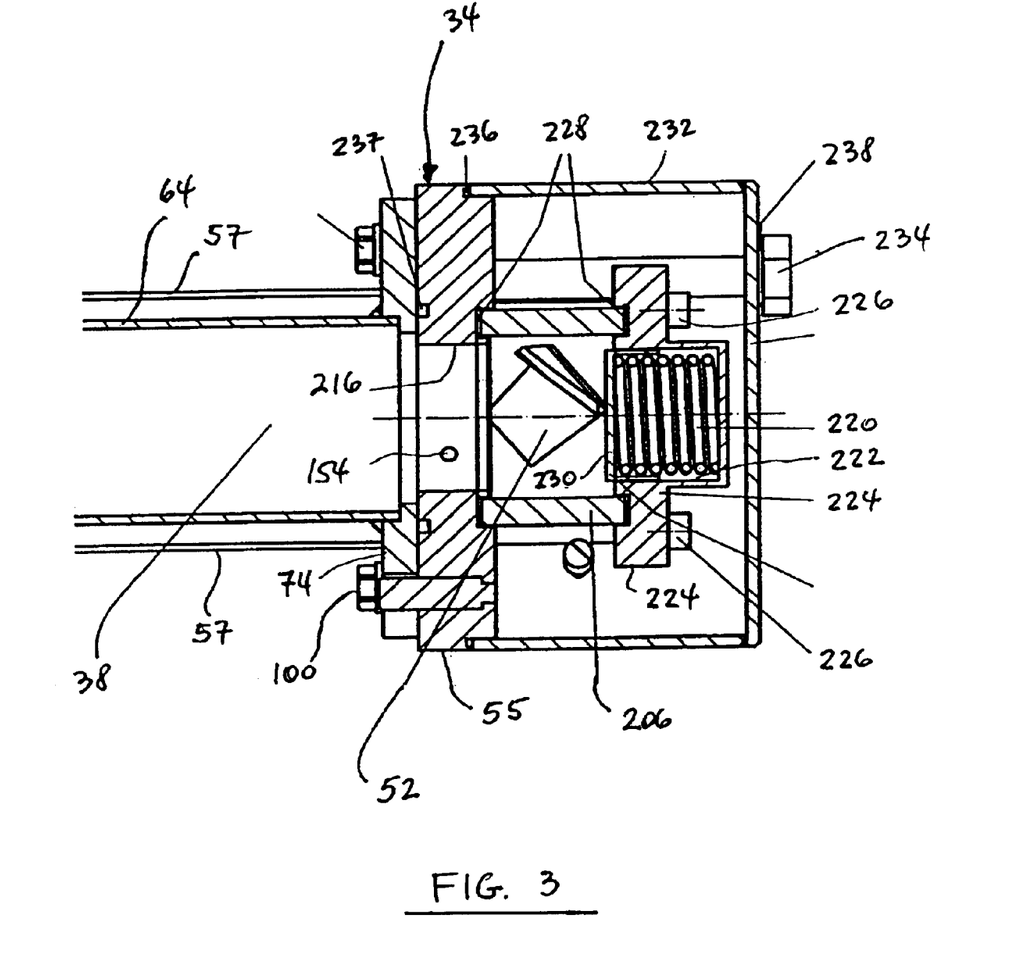
FIG. 3 is a section corresponding to FIG. 1C but to a further enlarged scale restricted to the region of the retroreflector.
Figure 4:
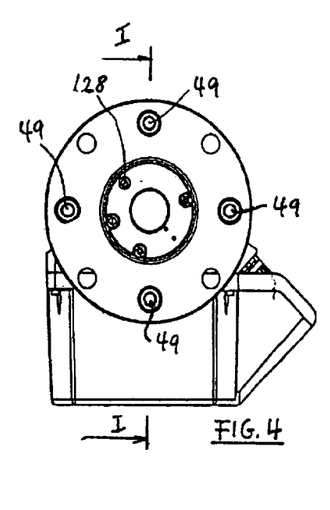
FIGS. 4 to 7 are cross-sections through the gas permeable probe of FIG. 1 taken along lines IV—IV, V—V, VI—VI and VII—VII respectively.

Turning now to FIGS. 1C and 3, the retroreflector arrangement at the second end 34 of the elongate hollow structure will now be described in more detail. As already mentioned, the connection flange 74 at the right-hand end of the filter support tube 64 is secured by screws 100 to the support member or flange 55, which is in turn connected via the tie members 57 to the first mounting flange 40 at the left-hand end 32 of the elongate hollow structure. As indicated in FIG. 6, the tie members 57 each have the form of an arcuate metal plate 61 with two tubes 63 and a stiffener 65 welded to it. The modular filter unit 54 can be inserted and removed through the spaces between the tie members 57 as indicated by the arrow 102. The tubes 201, 210 for the calibration gas and for the pressure sensor extending through respective ones of the tubes 63, as does the electrical lead 204 for the heater 206 associated with the retroreflector 52. This can be seen from the reference numerals 201, 210 and 204 entered in FIG. 6. The tube 201 for the calibration gas, which is also used for the neutral gas and the filter cleaning gas flow, opens via a passage 154 in the support member 55 and the orifice 154 into the optical cavity.

The support member 55 has a central opening 216 and acts at its end face 218 adjacent the central opening as a support for the open end of the retroreflector 52 which is formed in this embodiment as a corner reflector or triple reflector. If desired, a window can be provided in front of the retroreflector. The retroreflector is urged against the end face of the plate member by a compression coil spring 220 received in a pot-like recess 222 of a pressure disc or retention member 224 which is spaced from the plate member by the ring heater 206. Three bolts 226, of which two can be seen in FIG. 3, serve to connect the pressure disc to the support member 55, with the ring heater 206 acting as a spacer. Seals 228 are provided at the two axial ends of the ring heater 206 to ensure that a sealed arrangement is present. The compression coil spring acts on the retroreflector via a cup member or piston 230 which serves to distribute the load from the spring 220 on the retroreflector. The compression coil spring 220 is a resilient member which takes into account differential thermal expansion between the retroreflector 52 and the structure 55, 206, 224, 226 surrounding it. The arrangement comprising the retroreflector, the pressure disc and the coil spring and cup member is surrounded by an outer cover 232 which is secured to the plate member via two screws 234. This cover 232, provided with seals at 236 and 238, isolates the retroreflector assembly from the gases passing through the duct 48. A further graphite seal 237 is provided between the connection flange 74 and the support member 55 in a ring groove formed in the support member.

The entire gas permeable probe can be removed as a module from the duct or chimney by releasing the bolts 49. In addition, the module comprising the transceiver 20, the housing 26, the carrier tube 178, the ring plate 184 and the third mounting flange 170 can be removed from the modulator assembly comprising the second mounting flange 44, the support tube 42, the inner tube 116 and the elongate hollow structure 30 by releasing the bolts 191.

The filter module 54 comprising the connection flange 72, the flexible metallic bellows 70, the filter mounting tube 62, the filter tube member 56, the filter support tube 64 and the connection flange 74 can be removed as a unit from the gas permeable probe by releasing the screws 88 and 100 without distributing the remainder of the assembly. Once the filter module has been removed, the pressure ring 78 can also be withdrawn axially from the first mounting flange 40 and the optical window 50 can be readily removed and exchanged as can the ring seals 83 and 87.

In addition, the module formed by the retroreflector assembly can easily be dismantled by removing the screws 234 connecting the cover 232 to the plate member and subsequently removing the screws connecting the pressure disc 224 to the support member 55 so that the retroreflector 52 and/or the ring heater 206 and the seals 228 associated therewith can be removed and replaced as necessary. The module comprising the support member 55 and the connection structure 57 as well as the first mounting plate 40 forms a welded structure which remains together as a module.

The cover of the housing 26 can be removed whenever required, thus providing access to the power supply 132 and to the other items contained in the housing.

Because the inner tube 10 is sealed in use by the optical windows 172 and 50, there is no danger of it becoming contaminated internally, and therefore there is no danger of contamination having an unpredictable effect on the light used for the spectral analysis. The conduction of the sensor line 140, the pressure sensing line 210 and the gas conducting line 201 as well as the electrical leads 128, 204 within the intermediate space between the support tube 42 and the inner tube 116 ensures that substances evaporating from these components at the elevated temperature prevailing within the duct or chimney 48 do not contaminate the optical cavity or the interior of the inner tube 116 and therefore can also not affect the quality of the spectral analysis.

The gas permeable probe of the present invention has the following advantages and features which are united in the modulator design:

A large optical absorption path.
The design permits absorption paths of 1 m for the standard design and can be made longer or shorter depending on the requirements by substituting connection structures and filter structures of different lengths which are available as exchange modules.

Integrated temperature measurement for the gas temperature.
The measurement sensor is positioned in the exhaust gases flowing through the duct or chimney and is thus protected against any corrosive substances present in the flue gases. Because of its close proximity to the filter structure, the temperature measurement is representative of the temperature prevailing in the flue or duct at the filter structure and thus in the optical cavity. Alternatively, it is also possible to place the temperature measuring sensor in the optical cavity. However, the provision of the temperature measuring sensor outside the optical cavity facilitates the modular construction and the exchange of the filter module.

Integrated pressure measurement of the pressure in the duct or chimney.
The pressure of gas is measured in the measuring cavity and serves for the normalization of the measurement results, especially when calibration measurements are being carried out, since then the calibration gas flowing into the cavity can be set with a higher pressure and this higher pressure must be known for the correct determination of the calibration gas values.

Gas checking is possible.
The analyzers used with the gas permeable probe and the gas permeable probe can be checked with respect to their measurement functions by using calibration gases and neutral gases to ensure that they are functioning correctly. The gas examination can take place manually or automatically. The optical cavity can be used as a neutral path by blowing the volume of the optical measurement path free of other gases using air or $N_2$. This can take place at any time, the gas permeable probe does not need to be removed for this purpose, and the apparatus remains at its point of installation.

Use in pressurized systems is possible.
Since the optical measurement cavity is closed at one end by the optical window and at the other end by a retroreflector assembly, it can be designed for operation at elevated pressure, such as for example 2 bar. It is, however, necessary to ensure that the optical analyzer is calibrated for such pressures.

No NBR problems (Null-Punkt Reflektor=zero point reflector)
This advantage is achieved because the optical measurement path can be blown free of gases and thus filled with a neutral gas so that the zero point can be detected using the optical cavity filled with the neutral gas. It is thus possible to dispense with a separate zero point reflector. All the optical boundary surfaces which participate in the formation of the measured value are thus also involved in the zero point measurement and it is no longer possible for the measured values to be influenced by drifting of the zero point measurement.

Elimination of the sensitivity to dust.
Since dust can be separated out at the surface of the filter material it no longer affects the quality of the measurement, unless the measurement is intended to detect dust particles, in which case the pore size of the filter is selected to enable the dust particles of interest to enter the optical cavity.

It can be used at high dust concentrations.
The filters in the gas permeable probe can be designed to reliably keep dust out of the optical measurement cavity (by selection of the pore size of the filter) so that it can be ensured that dust does not influence the measurement result.

No specially routed flushing air system is required.
Since dust is essentially deposited on the filter it does not reach the optical boundary surfaces. Because no permanent flushing air supply is required, there is also no possibility of the flushing air giving rise to problems, in particular with small ducts.

No problem with external light sources.
Because the beam path used for the measurement is fully encapsulated, no external light can enter into the beam path.

Utilize action with unfavorable flow conditions.
The gas permeable probe can be used, when turbulence is present and at very low gas speeds.

It can be used with pressures which change significantly.
Because no flushing air is required, the gas permeable probe cannot be affected by flushing air. In conventional systems, which require flushing air, the flushing air supply must be laid out for the maximum operating pressure, and a lower operating pressures flushing air affects the measurement.

It can be used with high moisture contents.
By utilizing filter structures with a hydrophobic membrane and small pore sizes around 0.2 $\mu$m, water droplets can be kept out of the optical cavity. Only gaseous water enters into the measurement cavity and this at small time constants.

Matching of the optical absorption path to the gas concentration to be measured.
The length of the measurement cavity can be matched to the gas concentration to be measured, at low concentrations along the absorption paths that are required. At high concentrations shorter absorption paths are sufficient.

Exchange of the optical components in accordance with the required spectral range (ultraviolet to infrared).
The optical components that are required, that is, the windows and the retroreflector, can be matched to the required spectral range by choosing suitable materials and surfaces of the components.

Cross beam path for laser applications.
When used with a laser spectrometer the beam path in the measurement cavity is closed. This beam guidance prevents interference effects.

Supply of calibration gases.
Calibration gases and neutral gases can be connected to gas connecting fittings and directed into the optical cavity through gas conducting lines.

Calibration gas heating.
The gas conducting line is laid out so that the calibration gas or neutral gas is heated up to the temperature of the gas flow through the duct. The line leading into the optical cavity has direct contact to the exhaust gas in the duct. A body is preferably inserted into the gas conducting line which continually swirls the air (for example a bar with a spiral spring placed around it can be disposed inside the gas conducting line) and in this way the best possible contact of the gas molecules with the outer wall of the gas conducting line can be ensured. In this manner, the gas is heated up approximately to the gas temperature prevailing within the duct and the cross-section of the line can be designed such that a pressure pulse can also be effectively transmitted in order to free the outer surface of the filter from dust deposits. The gas conducting line can be the same line which serves to introduce calibration gases or neutral gases into the optical cavity or it can be a separate dedicated line.

Ceramic filters with inert behavior can be used which have no catalytic effect on the gases to be measured.

Ceramic filters can also be used with coatings of a PTFE material in order to repel liquid water while being simultaneously permeable to gas.

Compensation for different coefficients of expansion.
This is achieved, as explained, by the use of the membrane bellows which, for example, can take account of the different thermal expansion between the ceramic filter material and the stainless steel of the connecting structure.

Temperature range.
The temperature range can be up to and beyond 450° C. for dry applications. The temperature range can be at least up to 200° C. for wet applications. The maximum possible temperature at which the hydrophobic coating, for example the PTFE membrane, can be used is limited by the operating limit of PTFE and by the available seal materials.

Heatable optical boundary surfaces.
The use of heating for the optical boundary surfaces makes it possible to prevent them from misting up when the gas permeable probe is used, with intermittent operation, and at measurements close to the dew point. The optical boundary surfaces are heated to a temperature which is 55° C. higher than the local environment. From a temperature above 160° C. onwards, the heating can be switched off.

Separation of the constructional space for the guidance of leads and the optical beam path.
This separation makes it possible to avoid disturbing effects caused by foreign components. Thus contaminants on components and substances which are given off by the components are kept away from the optical cavity, so that they cannot affect the measurements.

A minimum number of seal locations relative to the medium flowing through the duct or chimney.
Because only a few seal positions are present the chances of leakage are minimized.

Integrated electronics for temperature and pressure measurement and for the monitoring of the operation of the gas permeable probe.

Integrated regulation system for the heating of the optical boundary surfaces with monitoring of their operation by means of current measurements.

Output of the measurement data and input of parameters for the gas permeable probe and measurement system via a field bus.

What is claimed is:

1. A gas permeable probe for use in an optical analyzer for an exhaust gas stream flowing through a duct or chimney, the probe comprising:

an elongate hollow structure having first and second ends and a side wall, with an optical cavity defined between said first and second ends within said side wall, a filter forming part of said elongate hollow structure, a mounting structure at said first end adapted for mounting said elongate hollow structure within said duct or chimney including a tube disposed within the mounting structure having first and second opposite ends, an optical window at said first end permitting a light beam originating from an optical analyzer to enter into said optical cavity to travel from said first end to said second end, said mounting structure comprising a first mounting flange at said first end of said elongate hollow structure, said first mounting flange containing said optical window, the probe further comprising a mating flange secured to said second opposite end of said tube and sealingly connected to said first mounting flange, a ring-shaped connecting member between said first mounting flange and said mating flange and a ring heater disposed around said connecting member, said mating flange being connected to said connecting member and said first mounting flange being connected to said connecting member, respective seals between said mating flange and said ring heater, between said ring heater and said connecting member, between said connecting member and said first mounting flange and between said first mounting flange and said optical window, and a retroreflector provided at said second end for returning said light beam to said first end of said hollow structure, wherein said first opposite end of the tube is located remote from said first end of said elongate hollow structure and is closed by a first window adapted to transmit said light beam from an optical analyzer into the tube and said second end of said tube is closed by said optical window adapted to transmit said beam of light from said tube into said optical cavity and said returned light beam from said optical cavity into said tube, said tube thereby defining a closed cavity, said closed cavity being one of an evacuated cavity and a cavity containing a neutral gas.

2. A gas permeable probe in accordance with claim 1, said mounting structure comprising a first mounting flange at said first end of said elongate hollow structure, a second mounting flange adapted for mounting to a wall of said duct of said chimney and a support tube extending from said second mounting flange to said first mounting flange.

3. A gas permeable probe in accordance with claim 2, there being a carrier for an optical analyzer extending away from said second mounting flange at a side of said second mounting flange remote from said first mounting flange to a third mounting flange at said first opposite end of said tube, said third mounting flange being adapted for the attachment of an optical analyzer positioned outside of said duct or chimney.

4. A gas permeable probe in accordance with claim 3, wherein a housing is provided on said carrier for said optical analyzer and contains at least one of:

a power supply including a lead for at least one heater associated with said gas measurement probe, a regulating circuit for regulating an operation of said at least one heater, at least one gas supply line for supplying at least one of a calibration gas, a neutral gas and a filter cleaning gas to said optical cavity, at least one pressure sensing line for sensing an operating pressure in or adjacent to said optical cavity, at least one temperature sensing line for sensing an operating temperature in or adjacent to said optical cavity.

5. A gas permeable probe in accordance with claim 4, wherein an intermediate space is formed between said support tube and said tube and all lines and leads associated with said gas measurement probe and extending to said first end of said elongate hollow structure or beyond said first end are routed through said intermediate space.

6. A gas permeable probe for use in an optical analyzer for an exhaust gas stream flowing through a duct or chimney, the probe comprising:

an elongate hollow structure having first and second ends and a side wall, with an optical cavity defined between said first and second ends within said side wall, a filter forming part of said elongate hollow structure, a mounting structure at said first end and adapted for mounting said elongate hollow structure within said duct or chimney, said mounting structure comprising a first mounting flange at said first end of said elongate hollow structure, a second mounting flange adapted for mounting to a wall of said duct of said duct or chimney and a support tube extending from said second mounting flange to said first mounting flange, an optical window at said first end permitting a light beam originating from an optical analyzer to enter into said optical cavity to travel from said first end to said second end, retroreflector provided at said second end for returning said light beam to said first end of said hollow structure, a tube disposed within said mounting structure and having first and second opposite ends, said first opposite end being located remote from said first end of said elongate hollow structure and being closed by a first window adapted to transmit said light beam from an optical analyzer into the tube and said second end of said tube being closed by a second window adapted to transmit said beam of light from said tube into said optical cavity and said returned light beam from said optical cavity into said tube, said tube thereby defining a closed cavity, said closed cavity being one of an evacuated cavity and a cavity containing a neutral gas, at least one gas supply line and at least one electrical power supply lead extending into the closed cavity, and an intermediate space being formed between said support tube and said tube and wherein the at least one line and at least one lead associated with said gas measurement probe extending to said first end of said elongate hollow structure or beyond said first end are routed through said intermediate space.

7. A gas permeable probe in accordance with claim 6, said second window being formed by said optical window.

8. A gas permeable probe in accordance with claim 6 wherein said first mounting flange contains said optical window, the probe further comprising a mating flange secured to said second opposite end of said tube and sealingly connected to said first mounting flange.

9. A gas permeable probe in accordance with claim 8, there being a ring-shaped connecting member between said first mounting flange and said mating flange and a ring heater disposed around said connecting member, said mating flange being connected to said connecting member and said first mounting flange being connected to said connecting member.

10. A gas permeable probe in accordance with claim 9, there being respective seals between said mating flange and said ring heater, between said ring heater and said connecting member, between said connecting member and said first mounting flange and between said first mounting flange and said optical window.

* * * * *